US00PP14484P29

(12) United States Plant Patent
van Rijn

(10) Patent No.: US PP14,484 P2
(45) Date of Patent: Jan. 27, 2004

(54) ANTHURIUM PLANT NAMED 'TENDER LOVE'

(50) Latin Name: *Anthurium andreanum*
Varietal Denomination: Tender Love

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 10/377,521

(22) Filed: Feb. 28, 2003

(51) Int. Cl.[7] ..... A01H 5/00
(52) U.S. Cl. ..... Plt./365
(58) Field of Search ..... Plt./365

*Primary Examiner*—Kent Bell
(74) *Attorney, Agent, or Firm*—C. A. Whealy

(57) ABSTRACT

A new and distinct cultivar of Anthurium plant named 'Tender Love', characterized by its upright and outwardly spreading plant habit; freely clumping growth habit; durable dark green leaves; dark pink and green bi-colored spathes with light orange-colored spadices that are positioned above and beyond the foliage on strong and erect scapes; freely flowering habit; and good inflorescence longevity.

2 Drawing Sheets

Botanical classification/cultivar designation: *Anthurium andreanum* cultivar Tender Love.

BACKGROUND OF THE INVENTION

The present invention relates to a new and distinct cultivar of Anthurium plant, botanically known as *Anthurium andreanum,* and hereinafter referred to by the name 'Tender Love'.

The new Anthurium is a product of a planned breeding program conducted by the Inventor in Schipluiden, The Netherlands. The objective of the program is to create and develop new compact, freely clumping and freely flowering Anthurium cultivars with strong roots, dark green leaves, attractive spathe color, and good inflorescence longevity.

The new Anthurium originated from a cross by the Inventor on Jan. 6, 1998 of a proprietary selection of *Anthurium andreanum* identified as code number 9608, not patented, as the female, or seed, parent with a proprietary selection of *Anthurium andreanum* identified as code number 9715, not patented, as the male, or pollen, parent. The cultivar Tender Love was discovered and selected by the Inventor as a plant within the progeny of the stated cross in a controlled environment in Schipluiden, The Netherlands in 1999.

Asexual propagation of the new cultivar by meristem culture in a laboratory in Belgium since November, 1999, has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Tender Love. These characteristics in combination distinguish 'Tender Love' as a new and distinct cultivar:

1. Upright and outwardly spreading plant habit.
2. Freely clumping growth habit.
3. Durable dark green leaves.
4. Dark pink and green bi-colored spathes with light orange-colored spadices that are positioned above and beyond the foliage on strong and erect scapes.
5. Freely flowering habit.
6. Good inflorescence longevity.

Plants of the new Anthurium can be compared to plants of the female parent, the proprietary selection identified as code number 9608. In side-by-side comparisons conducted in Schipluiden, The Netherlands, plants of the new Anthurium differed from plants of the selection 9608 in the following characteristics:

1. Plants of the new Anthurium were bushier than plants of the selection 9608.
2. Leaves of plants of the new Anthurium were larger than and not as hard as leaves of plants of the selection 9608.

Plants of the new Anthurium can be compared to plants of the male parent, the selection 9715. In side-by-side comparisons conducted in Schipluiden, The Netherlands, plants of the new Anthurium differed from plants of the selection 9715 in the following characteristics:

1. Leaves of plants of the new Anthurium were stronger than leaves of plants of the selection 9715.
2. Plants of the new Anthurium had dark pink and green bi-colored spathes whereas plants of the selection 9715 had white, red and green tri-colored spathes.

Plants of the new Anthunium differ primarily from plants of the cultivar 1999-22, disclosed in U.S. Plant patent application Ser. No. 10/377,497 filed concurrently, in spathe and spadix coloration.

Plants of the new Anthurium can also be compared to plants of the cultivar Sugar Love, disclosed in U.S. Plant Pat. No. 10,998. In side-by-side comparisons conducted in Schipluiden, The Netherlands, plants of the new Anthurium differed from plants of the cultivar Sugar Love in the following characteristics:

1. Plants of the new Anthurium grew faster than plants of the cultivar Sugar Love.

2. Plants of the new Anthurium were not as bushy as plants of the cultivar Sugar Love.
3. Leaves of plants of the new Anthurium were darker green in color than leaves of plants of the cultivar Sugar Love.
4. Spathes of plants of the new Anthurium were darker pink in color than spathes of plants of the cultivar Sugar Love.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a side perspective view of a typical flowering plant of the cultivar Tender Love.

The photograph on the second sheet comprises a close-up view of a typical inflorescence of 'Tender Love'.

DETAILED BOTANICAL DESCRIPTION

In the following description, color references are made to The Royal Horticultural Society Colour Chart, 2001 Edition, except where general terms of ordinary dictionary significance are used. The aforementioned photographs and the following observations and measurements describe 10-month old plants grown in 14-cm containers in Schipluiden, The Netherlands, in a glass-covered greenhouse with an average day temperature of 23° C., an average night temperature of 21° C. and light levels about 6 kilolux.

Botanical classification: *Anthurium andreanum* cultivar Tender Love.

Parentage:

*Female parent.*—Proprietary selection of *Anthurium andreanum* identified as code number 9608, not patented.

*Male parent.*—Proprietary selection of *Anthurium andreanum* identified as code number 9715, not patented.

Propagation:

*Method.*—By meristem culture.

*Time to initiate roots on a meristem-cultured plant.*—About 28 days at 24° C.

*Time to develop roots on a meristem-cultured plant.*—About 270 days at 24° C.

*Root description.*—Thick, fleshy, dark pink to cream-colored; lateral roots, abundant.

Plant description:

*Plant shape.*—Upright and outwardly spreading plant habit, narrow inverted triangle, symmetrical.

*Growth habit.*—Freely clumping, bushy and dense growth habit; about ten clumps per plant. Appropriate for 14-cm containers; moderately vigorous.

*Plant height, from soil level to top of leaf plane.*—About 36 cm. Plant height, from soil level to top of inflorescences: About 38 cm.

*Plant diameter or spread.*—About 48 cm.

*Crop time.*—About 10 months are usually required from planting of young plants to finished plants in a 14-cm container.

*Foliage description.*—Arrangement: Alternate; simple. Quantity per plant: About 60. Length: About 16.6 cm. Width: About 10.3 cm. Shape: Deltoid. Apex: Apiculate. Base: Cordate. Margin: Entire. Texture, upper and lower surfaces: Leather; glabrous, smooth; durable. Venation pattern: Pinnate. Color: Young leaves, upper surface: Darker than 152A. Young leaves, lower surface: Slightly darker than 152A. Mature leaves, upper surface: 147A. Mature leaves, lower surface: Slightly more green than 146A to 146B. Venation, upper surface: 144A. Venation, lower surface: 144B. Petiole: Length: About 26 cm. Diameter, just below geniculum: About 3.5 mm. Diameter, at plant base: About 7 mm. Texture: Smooth. Color: 146B to 146C. Geniculum length: About 1.7 cm. Geniculum diameter: About 4 mm. Geniculum color: 144A. Wing length: About 2.7 cm. Wing diameter: About 4 mm. Wing color: 157B.

Inflorescence description:

*Inflorescence arrangement.*—Spathes with spadices held above and beyond the foliage. Flowering structures arise from leaf axils. Freely and continuous flowering during the autumn in Schipluiden, The Netherlands. Typically about 14 inflorescences per plant. Inflorescences not fragrant.

*Inflorescence longevity.*—Inflorescences last about two months under winter conditions and about three months under summer conditions; inflorescences persistent.

*Spathe.*—Length: About 7.6 cm. Width: About 8 cm. Shape: Broadly deltoid to cordate. Apex: Cuspidate to mucronulate. Base: Cordate. Margin: Entire. Texture, upper and lower surfaces: Leathery; glabrous, smooth. Aspect: Moderately cupped. Color: When opening, front surface: 51A to 51B; towards the base, 143A to 143B. When opening, back surface: 51C to 54C; basal margins tinged with 143C. Fully developed, front surface: 51A to 51B; towards the base, 143B to 144A to 144B. With development, 54A; towards the base, 143A. Fully opened, back surface: 51D to 54D; towards the base, 147C.

*Spadix.*—Length: About 3.4 cm. Diameter: About 7 mm. Shape: Columnar, tapering towards the apex; apex, obtuse. Cross section: Rounded. Aspect: About 20° from vertical. Color: Immature: 32C to 33C. Mature: 33D.

*Flowers.*—Quantity per spadix: Numerous, about 150. Shape: Rounded. Height: Less than 0.5 mm. Diameter: About 0.8 mm.

*Reproductive organs.*—Androecium: Anther color: 11D. Amount of pollen: Scarce. Pollen color: 11C. Gynoecium: Stigma shape: Ovoid. Stigma color: 157D. Ovary color: 157D.

*Scape.*—Length: About 29 cm. Diameter: About 4 mm. Strength: Strong. Aspect: Erect to slightly outwardly slanted, about 30° from vertical. Color: 146A to 146B.

*Seed and fruit.*—Seed and fruit development has not been observed on plants of the new Anthurium.

Disease/pest resistance: Under commercial production conditions, plants of the new Anthurium have not been observed to be resistant to pathogens or pests common to Anthurium.

Temperature tolerance: Plants of the new Anthurium have been observed to tolerate temperatures from 14 to 35° C.

It is claimed:

1. A new and distinct cultivar of Anthurium plant named 'Tender Love', as illustrated and described.

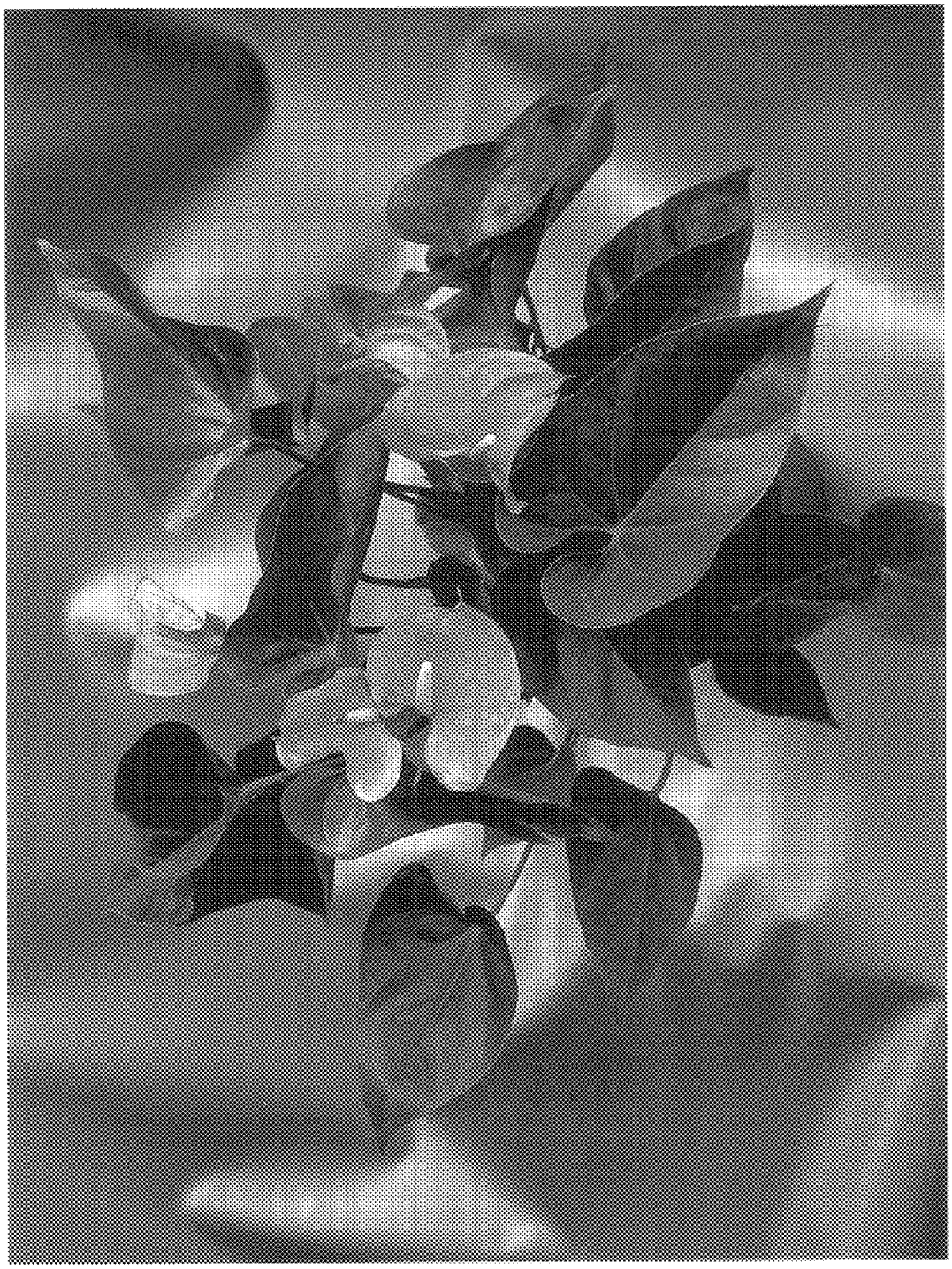

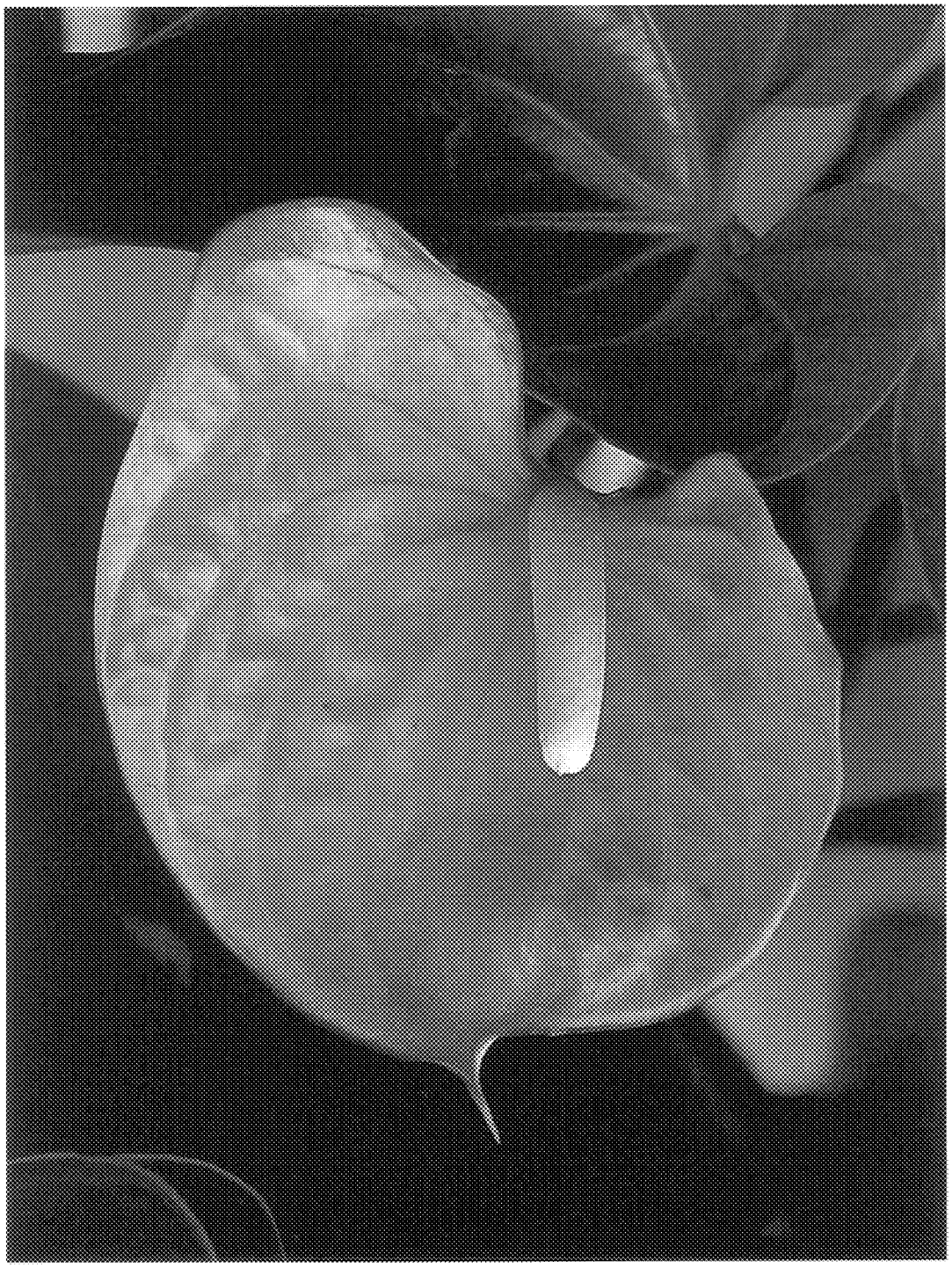

* * * * *